United States Patent [19]

Lockerby et al.

[11] 4,130,012

[45] Dec. 19, 1978

[54] SOIL MOISTURE INDICATOR

[75] Inventors: Charles E. Lockerby, Foster City; W. Scott Dimmick, Sunnyvale, both of Calif.

[73] Assignee: Design Loft Creations, Inc., Foster City, Calif.

[21] Appl. No.: 854,794

[22] Filed: Nov. 25, 1977

[51] Int. Cl.² ............................................. G01N 5/02
[52] U.S. Cl. .............................. 73/73; 116/114 AM; 116/118 A; 422/55
[58] Field of Search ....... 73/73; 116/114 AM, 118 A, 116/DIG. 7; 23/253 TP

[56] References Cited

U.S. PATENT DOCUMENTS

| | | | |
|---|---|---|---|
| 3,019,638 | 2/1962 | Klein | 73/73 |
| 3,702,755 | 11/1972 | Palmer | 116/114 AM X |
| 3,824,844 | 7/1974 | Strickland | 73/73 |
| 3,881,873 | 5/1975 | Klowden | 73/73 X |
| 3,951,098 | 4/1976 | Meyers | 116/114 AM |
| 4,020,785 | 5/1977 | Palmer | 73/73 X |
| 4,063,452 | 12/1977 | Bradshaw | 73/73 |

*Primary Examiner*—Charles Gorenstein
*Attorney, Agent, or Firm*—Thomas H. Olson

[57] ABSTRACT

A soil moisture indicator including a rigid planar base member having sufficient strength to permit its partial insertion into soil adjacent growing plants and a water absorbent member, such as blotter paper, secured to the base member. Overlying the water absorbent sheet adhesively secured thereto is a transparent water impervious layer, the layer having an increment extending beyond the longitudinal extremities of the water absorbent sheet, the incremental portions being adhesively secured to the base member so that abrasive forces on the water absorbent sheet during insertion into the soil are avoided. An improved method for manufacturing the devices in a highly efficient and automated fashion.

4 Claims, 5 Drawing Figures

U.S. Patent  Dec. 19, 1978  4,130,012
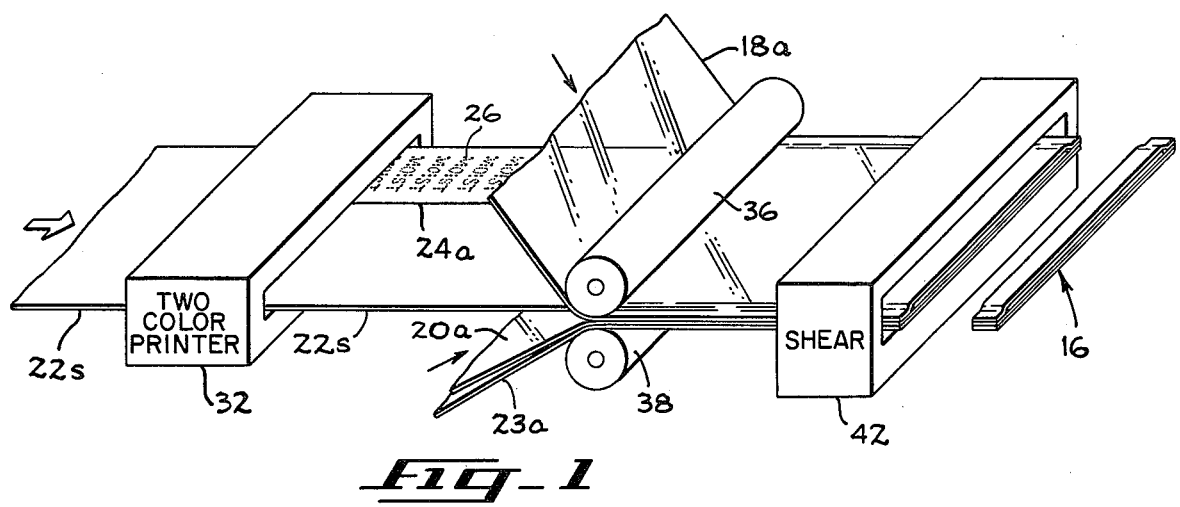
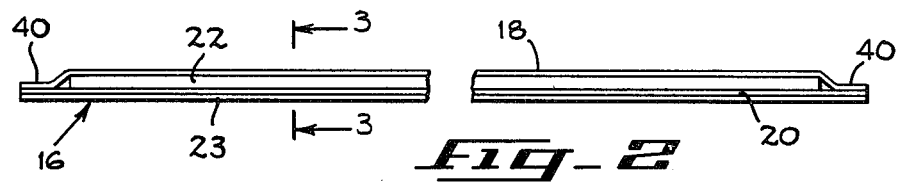
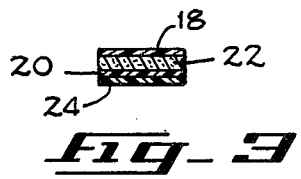
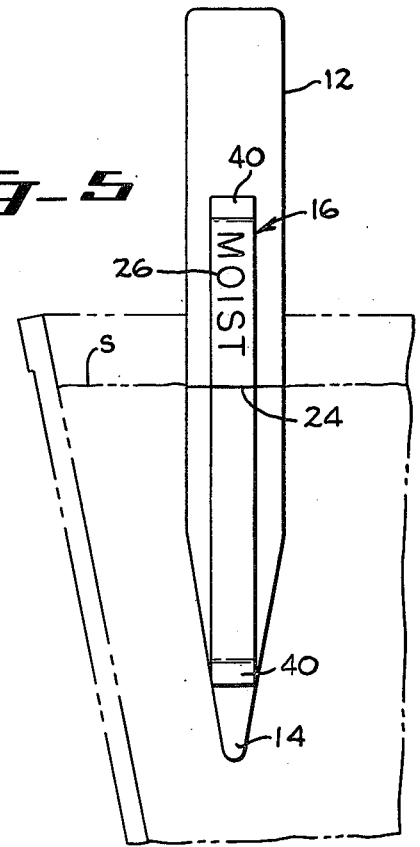
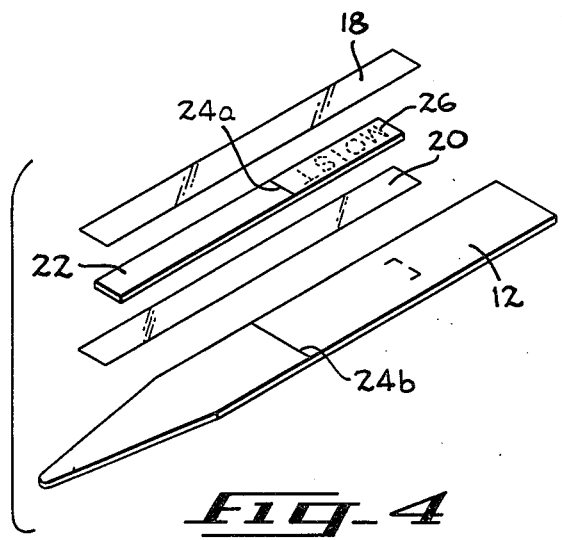

SOIL MOISTURE INDICATOR

BACKGROUND OF THE INVENTION

1. Field of the Invention

This invention relates to soil moisture indicators and particularly to soil moisture indicators that are completely passive and are particularly suited for use in potted plants.

2. Description of the Prior Art

U.S. Pat. No. 3,019,638 and 3,824,844 (73/73) disclose soil moisture monitors which in construction and operation are different from the present invention but which are intended to achieve a purpose generally similar to that achieved by the present invention.

U.S. Pat. No. 3,881,873 (23/253 TP) discloses a moisture indicating probe and a method of use which also is designed to achieve the same purpose as the present invention but which employs completely different principles of operation.

More than a year before the filing date hereof there has been on sale in the United States of America a device composed of a rigid body having sufficient strength to afford insertion thereof into soil and a water sensitive sub-assembly adhesively secured to said rigid member that is composed of a central layer of blotter paper laminated on opposite surfaces with congruent transparent sheets. The transparent sheets are glued to the blotter paper and the lower transparent sheet is in turn glued to the rigid body. The devices that have been on sale operate satisfactorily when new but have a relatively short life because the blotter paper, particularly when it is wet, tends to delaminate so that the device is subject to delamination. Delamination is likely to occur upon insertion of the device into the soil surface.

SUMMARY OF THE INVENTION

A moisture indicator incorporating the present invention includes a sheet of blotter paper laminated between two layers of transparent water impervious material. The transparent layers have a width equal to that of the blotter layer but a length greater than that of the blotter layer so that the active element can be secured to the rigid base member at the ends as well as throughout the inner surface of the lower layer to the end that the strength and longevity of the device is increased substantially. Thus, even when the blotter paper is weakened by being wet, it is not liable to damage because the extending end portions of the transparent layers retain it firmly to the rigid backing member.

Thus it is an object of the invention to provide a moisture indicator having superior longevity to those previously available. This object is achieved by providing relatively strong transparent impervious layers between which the blotter sheet is laminated and providing longitudinal extensions or increments on the water impervious layers that extend beyond the longitudinal extremity of the blotter sheet.

Another object is to provide a method for manufacturing indicators embodying the invention which affords rapid and automated production.

The foregoing, together with other objects, features and advantages will be more apparent after referring to the following specification and the accompanying drawings.

BRIEF DESCRIPTION OF THE DRAWINGS

FIG. 1 is a partially schematic view in perspective of apparatus for manufacturing moisture indicators according to the invention and depicting the method of the invention.

FIG. 2 is a longitudinal side view of the active element of the moisture indicator embodying the invention.

FIG. 3 is a cross sectional view taken along line 3—3 of FIG. 2.

FIG. 4 is an exploded view in perspective of the parts constituting a moisture indicating device of the invention.

FIG. 5 is a side view of a moisture indicator embodying the invention in place in potted soil.

DESCRIPTION OF THE PREFERRED EMBODIMENT

Referring more particularly to the drawings and to FIG. 5, reference numeral 12 indicates an elongate rigid base member formed of material having sufficient strength to permit its penetration into plant growing media such as soil S. Base member 12 can be formed of plastic sheet having a thickness of 0.025 inches more or less, of wood in a form conventionally seen in nurseries for identifying potted plants, or of another material having adequate strength and rigidity. Base member 12 has a lower end 14 which is tapered to facilitate insertion of the same into soil S.

Adhesively secured to one surface of base member 12 is a moisture sensitive element identified generally at 16. Moisture sensitive element 16 includes an upper layer 18 and a lower layer 20 which are formed of water impervious transparent material such as 5 mil mylar or the like. Sandwiched between the upper and lower layers is a sheet of water absorbent material 22 which can be conventional green blotter paper having a thickness of about 20 mils. The surfaces of transparent layers 18 and 20 that contact water absorbent sheet 22 are provided with suitable adhesive so that the members are firmly laminated to one another. The outer or lower surface of layer 20 is provided with adhesive transfer tape 23 which is a water proof product having adhesive on both surfaces, the upper surface adhering to layer 20 and the lower surface adhering to base member 12. A suitable adhesive transfer tape is sold by the 3M Company under the designation 3M-467.

Because impervious layers 18 and 20 have a width equal to that of absorbent sheet 22, the lateral edges of the water absorbent sheet are exposed to soil S. Accordingly, when soil S is moist, absorbent layer 22 becomes moist and such moisture is transmitted by capillary action throughout the length of the water absorbent layer. Sheet 22 and base member 12 are provided with aligned transversely extending lines 24a and 24b, respectively, which lines form an indicium 24 for indicating the depth to which the device should be inserted into soil S in order to position a part of moisture sensitive element 16 below the surface of the soil and a part of the element above the surface. A region of water absorbent layer 22 in the part of element 16 above the surface of soil S is treated so as to produce a visual effect when wet different from that produced when dry.

Such treated region of the water absorbent layer is identified at 26. In the form of the invention shown in the drawing the treated area is in the form of the word "moist". The treated area is formed by waterproofing a region of the layer 22 so that such region will not absorb water even when the balance of water absorbent sheet 22 is wet. Because the treated region stays dry, its color remains constant irrespective of the water content of absorbent layer 22, whereas the balance of the water absorbent layer is relatively light when dry and relatively dark when wet. Accordingly, when absorbent sheet 22 is dry the treated region is invisible, and when the absorbent sheet is wet, the treated region is visible because of contrast between the wet and dry colors of the absorbent layer.

The method for forming moisture sensitive element 16 is depicted schematically in FIG. 1. A strip 22s of blotter paper or like absorbent layer is provided, such strip having a width equivalent to the length of water absorbent layer 22. Strip 22a of water absorbent material is fed through a two color printer 32 which prints in a color that contrasts with that of layer 22 a line 24a which coincides with insertion level indicium 24. The printer also forms treated area 26 in each of a series of recurring zones that extend transversely of strip 22s. A pattern, e.g. the word "moist", of the water proof region is formed by imprinting on strip 22s such pattern with a water proof material such as a hydrophic fluoroaliphatic resin which is diluted so as to be transparent and invisible. One material particularly suitable for printing is a material sold by the 3M Company under the trade designation FC-805. Accordingly, when the strip 22s exits printer 32 it has formed therein in transversely extending zones a series of recurring water proof patterns and a line 24a in contrasting color that coincides with insertion level indicium 24 on the water sensitive element 16.

Next the strip is conveyed to a roll station formed by an upper pressure roll 36 and a lower pressure roll 38. Fed into the roll station from above is a sheet of transparent water impervious material 18a. Fed into the roll station from below is a layer 20a of the same water impervious transparent material as well as a layer of adhesive transfer tape 23a. The surfaces of layers 18a and 20a that face absorbent strip 30 are pretreated with a thermo setting adhesive; pressure rolls 36 and 38 are heated so that, as the layers of material pass the roll station formed by the upper and lower rolls, a laminated assemblage is formed, the assemblage being shaped in a direction transverse of the path of forward movement as seen in FIG. 2.

The widths of transparent layers 18a and 20a are equal to one another and are greater than the width of absorbent strip 22a so that incremental portions of the transparent layers extend beyond the edge of the absorbent layer. Such incremental portions are identified in FIGS. 2 and 5 at 40. Because no absorbent material is interposed between the layers at incremental portions 40, the layers are adhesively bonded together very firmly.

When the laminated assemblage exits the roll station formed by rolls 36 and 38 it is conveyed through a shear 42 so that individual moisture sensitive elements 16 are produced.

The individual moisture sensitive elements are installed on respective base members 12 by pealing the peal off layer from the outer surface of adhesive transfer tape 23, line 24a on the element being aligned with line 24b on the base member and the water proofed area 26 being positioned remote from point 14. Moisture sensitive element 16 is pressed into adhesive contact with the base member to achieve a permanent adhesive connection between the element and the base member. Thus the lower surface of transparent layer 20 including incremental portions 40 are continuously adhesively joined to the base member. Consequently when the article is introduced into soil S, the integrity of the device will be maintained even though absorbent layer 22 may be weakened by moisture or the like.

The fabrication of elements 16 will be recapitulated after which the operation of the moisture indicator will be explained in somewhat more detail.

In one specific device designed according to the present invention strip 22s has a width of approximately 2 and fifteen/sixteenths inches (about 75 mm.) and transparent layers 18a, 20a and 23a have a width of about 3 and three/sixteenths inches (about 82 mm.). Absorbent layer 22s is first fed through printer 32 and recurrent water proof patterns 26 are printed thereon at intervals of approximately one-fourth inch (about 7 mm.) in width. Line 24a is also printed. At the roll station formed by rolls 36 and 38 layers 18a, 20a and 23a are fed in and laminated to one another and to absorbent strip 22a, the heat present in the pressure rolls activating the adhesive on the transparent layers. Finally, the laminated assemblage is severed into individual moisture sensitive elements 16 which have a cross section as shown in FIG. 3 so that the transverse edges of absorbent layer 22 are exposed. Finally, the moisture sensitive elements are installed onto base member 12 and the article is completed.

In use, the base member is inserted into soil S, the tapered configuration of end 14 facilitating entry of the device into the soil. Insertion level indicium 24 is aligned with the surface of soil S. Because incremental extensions 40 of the moisture sensitive element are securely adhered to the base member, the moisture sensitive element does not separate from the base member upon such insertion or subsequent thereto. Moisture within the soil contacts the exposed edges of absorbent strip 22 and migrates throughout the strip due to capillary action. When the absorbent strip becomes moist the color thereof darkens so that the water proofed pattern 26 becomes visible because it remains dry. When the water proof pattern is no longer visible, such indicates that absorbent layer 22 is dry which in turn indicates that soil S is dry, thereby indicating the need to add water to the soil.

Thus it will be seen that the present invention provides a soil moisture indicator which is sturdy, easy to use and of relatively low cost. Moreover, the method for fabricating the moisture responsive element 16 guarantees uniformity, low cost and satisfactory longevity of the device. Although one embodiment of the invention has been shown and described it will be obvious that other adaptations and modifications can be made without departing from the true spirit and scope of the invention.

What is claimed is:

1. An article of manufacture for indicating the moisture content of a plant growing medium comprising an elongate rigid base member having sufficient strength for penetration into the surface of said medium, an elongate water absorbent sheet having length and width dimensions less than corresponding dimensions of said base member, a transparent impervious layer laminated to one surface of said sheet, said layer having a width substantially equal to that of the sheet and a length greater than the length of the sheet so as to form an incremental portion of at least one longitudinal end of said sheet that extends beyond said sheet, means for adhesively securing said sheet and said incremental portion to said base member so that said layer overlies said sheet, and a region of said water absorbent sheet remote from said incremental portion being treated to produce a visual effect when said sheet is wet different from that produced when dry.

2. An article according to claim 1 including a second incremental portion integral with said layer and extending beyond said sheet at the end thereof opposite from first said incremental portion and means for adhesively securing said second incremental portion to said base member.

3. An article according to claim 1 including a second waterproof layer substantially congruent to first said layer and having one surface adhesively secured to said water absorbent sheet opposite first said layer, said second layer having an incremental portion in registry with the incremental portion of first said layer, said adhesively securing means including means for adhesively joining said incremental portions and means for adhesively securing said second layer to said base member.

4. An article according to claim 3 wherein both said waterproof layers include incremental portions that extend beyond the opposite end of said water absorbent sheet and means for adhesively securing last said incremental portions to one another and to said base member.

* * * * *